United States Patent [19]

Ushizawa et al.

[11] Patent Number: 4,582,589
[45] Date of Patent: Apr. 15, 1986

[54] PH SENSOR

[75] Inventors: Norihiko Ushizawa, Fujinomiya; Tsutomu Murakami, Ueno; Takeshi Shimomura, Fujinomiya; Noboru Oyama, Tokyo, all of Japan

[73] Assignee: Terumo Kabushiki Kaisha, Tokyo, Japan

[21] Appl. No.: 749,190

[22] Filed: Jun. 26, 1985

[30] Foreign Application Priority Data

Jun. 30, 1984 [JP] Japan ................... 59-136339

[51] Int. Cl.$^4$ ............................................ G01N 27/30
[52] U.S. Cl. ...................... 204/433; 204/416; 204/418; 324/438
[58] Field of Search ............... 204/403, 415, 416, 418, 204/433; 324/438

[56] References Cited

U.S. PATENT DOCUMENTS

| 3,869,354 | 3/1975 | Montaliro, Jr. ............. 204/415 X |
| 4,148,305 | 4/1979 | Reichenberger ............. 204/415 X |
| 4,271,002 | 6/1981 | Hawkins ..................... 204/418 |
| 4,273,636 | 6/1981 | Shimada et al. .............. 204/415 |
| 4,454,007 | 6/1984 | Pace .......................... 204/416 X |
| 4,492,622 | 1/1985 | Kuypers ..................... 204/415 X |

Primary Examiner—Andrew H. Metz
Assistant Examiner—Nam X. Nguyen
Attorney, Agent, or Firm—Frishauf, Holtz, Goodman & Woodward

[57] ABSTRACT

A pH sensor includes a substrate formed of an electrically conductive carbon material. A hydrogen ion-sensitive layer is formed on the substrate surface. The layer is formed of an electrooxidation polymer of a nitrogen-containing aromatic compound selected from the group consisting of 1-aminopyrene and a mixture of 1-aminopyrene and pyridine.

9 Claims, 6 Drawing Figures

F I G. 3
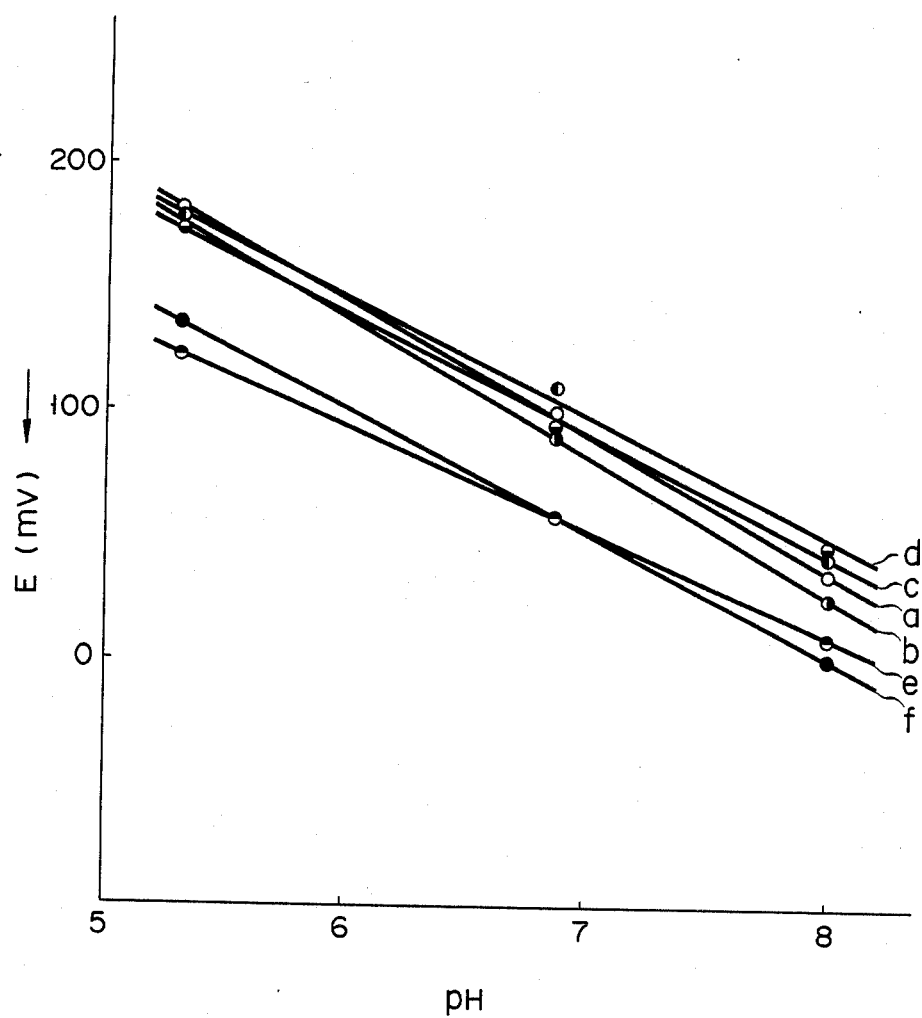

PH SENSOR

BACKGROUND OF THE INVENTION

1. Field of the Invention

This invention relates to a pH sensor, particularly, to a pH sensor of the so-called polymer film-coated electrode type.

2. Description of the Prior Art

A pH sensor of the type wherein the surface of an electrode formed of an electrically conductive material is coated with a hydrogen ion-sensitive polymer film is under development. Said pH sensor mentioned is used for measuring, for example, the hydrogen ion concentration of an aqueous solution by utilizing a potential response. A known pH sensor of this type comprises an electrode formed of a noble metal, particularly, platinum and coated with a polymer film, e.g., a film of polymer of phenol, diaminobenzene or the like. This pH sensor can be miniaturized, exhibits a rapid response time and, thus, is expected to be capable of insertion into a living body for measuring the pH of a body fluid. However, where the solution to be measured contains additional components such as micro ions, organic acids, basic compounds, medium molecular weight compounds (e.g., proteins and cleatinin) and nucleic acids (e.g., purines) as well as hydrogen ions, the pH sensor mentioned above tends to be affected by the additional components. Also, where dissolved oxygen is present in the solution to be measured, the potential value tends to fluctuate under the influence of the dissolved oxygen. The difficulty is thought to be derived from the use of a noble metal such as platinum, which is highly sensitive to oxygen, as the electrode substrate.

SUMMARY OF THE INVENTION

An object of the present invention is to provide a pH sensor comprising a polymer layer-coated electrode, which permits measuring the pH value of a solution without being influenced by interfering components contained in the solution.

The present inventors have found that an electrically conductive carbon material is unlikely to be affected by oxygen. Based on this finding, the inventors have conducted extensive research on the hydrogen ion-sensitive polymer layer which should be formed on the substrate consisting of a conductive carbon material. It has been found that an electrooxidation polymer layer of 1-aminopyrene or a mixture of 1-aminopyrene and pyridine achieves a rapid potential response to the hydrogen concentration of a solution, leading to the present invention.

According to the present invention, there is provided a pH sensor comprising a substrate formed of an electrically conductive carbon material, and a hydrogen ion-sensitive layer formed on the substrate surface, said film being formed of an electrooxidation polymer of a nitrogen-containing aromatic compound selected from the group consisting of 1-aminopyrene and a mixture of 1-aminopyrene and pyridine.

It is particularly desirable for the hydrogen ion-sensitive layer to be formed of an electrooxidation copolymer consisting of 1-aminopyrene and pyridine having a molar ratio of 1:1. The term "hydrogen ion-sensitive" used herein represents that a potential difference relative to a reference electrode is generated in response to the hydrogen ion concentration of an aqueous solution.

BRIEF DESCRIPTION OF THE DRAWINGS

FIGS. 3-6 show the characteristics of pH sensors of the present invention.

DETAILED DESCRIPTION OF THE PREFERRED EMBODIMENT

Figure 1:
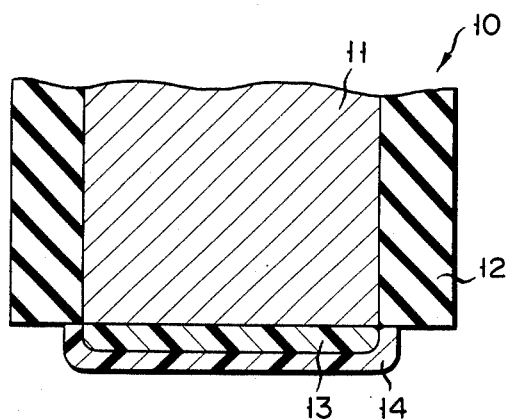
FIG. 1 is a cross sectional view showing a part of a pH sensor according to one embodiment of the present invention.

As seen from FIG. 1, a pH sensor 10 of the present invention comprises a substrate 11 formed of an electrically conductive carbon material. The conductive carbon material forming the substrate 11 is not particularly restricted. But, it is desirable to use a basal plane pyrolytic graphite for forming the substrate 11. The substrate 11, which may be optionally shaped, is linear in the pH sensor shown in FIG. 1.

The outer surface of the substrate 11 except the tip region is covered with an insulating layer 12 formed of, for example, a fluororesin. The exposed tip end surface of the substrate 11 is coated with a hydrogen ion-sensitive layer 13. The layer 13 is formed of an electrooxidation polymer of a nitrogen-containing aromatic compound (monomer) selected from the group consisting of 1-aminopyrene and a mixture of 1-aminopyrene and pyridine. In other words, the layer 13 is formed of an electrooxidation homopolymer of 1-aminopyrene or an electrooxidation copolymer of 1-aminopyrene and pyridine.

The electrooxidation polymerization for forming the hydrogen ion-sensitive layer 13 on the surface of the substrate 11 is carried out within a solution prepared by dissolving 1-aminopyrene together with or without pyridine, as desired, in an organic solvent, e.g., acetonitrile, which contains a supporting electrolyte, e.g., sodium perchlorate. The monomer concentration of the solution is between 1 m mole/l and 0.5 mole/l for aminopyrene, and between 1 m mole/l and 0.5 mole/l for pyridine. Specifically, the substrate 11, which acts as a working electrode, is immersed in the solution together with a reference electrode and a counter electrode. Under this condition, a suitable voltage, which is generally +1 V, is applied to the working electrode relative to the reference electrode so as to achieve the desired electrooxidation polymerization. Where the hydrogen ion-sensitive layer 13 is formed of the copolymer, the ratio of pyridine to 1-aminopyrene, which is not particularly restricted, is generally at most 10. It is particularly desirable for the layer 13 to be formed of an electrooxidation copolymer consisting of the same molar amount of 1-aminopyrene and pyridine because the influence on the hydrogen ion-sensitive layer 13 caused by the interfering components contained in the solution to be measured can be particularly suppressed when using this particular copolymer film. The thickness of the film 13 is generally between 1 μm and 1 mm.

The hydrogen ion-sensitive layer as formed by the electrooxidation polymerization is an oxidized form. If the hydrogen ion-sensitive layer is subjected to reducing conditions (e.g., application of minus voltage to the layer), the oxidized form can be converted into a reduced form to some extent, namely the ratio of the oxidized form to the reduced form in the layer may be varied. By post-treating the layer as formed to vary the ratio in question, the influence of interfering components on the layer can be further suppressed as compared to the layer in oxidized form. For example, the layer 13 can be reduced, if a constant voltage of −0.5 V (vs, SSCE) is applied to the layer 13 for about 10 minutes.

The hydrogen ion-sensitive layer 13 may be covered with a protection layer 14, as desired. The protection layer 14 prevents the hydrogen ion-sensitive layer from peeling from the substrate, and also prevents large and medium molecular weight compounds (e.g., proteins and sugars) from being absorbed on the hydrogen ion-sensitive layer thereby influencing the electromotive force. The protection layer 14 is capable of transmitting hydrogen ions, and preferably has a thickness of 0.1 μm to 300 μm. The protection layer 14 may be formed of, for example, poly (hydroxyethyl methacrylate), nitro cellulose, acetyl cellulose, regenerated cellulose, or polycarbonate.

Figure 2:
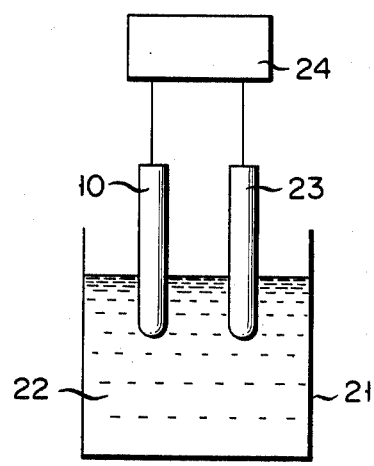
FIG. 2 schematically shows a pH measuring apparatus having the invented pH sensor incorporated therein.

FIG. 2 shows how to measure the pH value of a solution by using the pH sensor 10 shown in FIG. 1. It is seen that the pH sensor 10 is immersed in a solution 22 housed in a vessel 21 together with a reference electrode 23, e.g., a silver-silver chloride electrode or a saturated calomel electrode. The pH sensor 10 and the reference electrode 23 are connected to a potentiometer 24 so as to measure the potential difference between the pH sensor 10 and the reference electrode 23, i.e., the electromotive force of the pH sensor 10 relative to the reference electrode 23. It is possible to know the pH value of the solution 22 by applying the electromotive force thus detected to a calibration curve prepared in advance between the electromotive force and the pH value. In short, the pH sensor of the present invention exhibits a potential response to the pH value of a solution, particular, an aqueous solution. In other words, the pH value is detected in terms of the electromotive force of the pH sensor.

EXAMPLE

The surface of a basal plane pyrolytic graphite disc was cleaved off by a sharp knife so as to prepare a substrate having a fresh surface. The substrate except for the fresh surface was covered with a heat shrinkable tube for the purpose of insulation such that the lower end of the tube was flush with the surface of the substrate. Then, mercury was put in the tube, with a lead wire immersed in the mercury, so as to prepare a mercury contact electrode. A three-electrode cell was prepared by using the mercury contact electrode as a working electrode, together with a saturated sodium chloride calomel electrode, hereinafter referred to as SSCE, used as a reference electrode and a platinum mesh used as a counter electrode.

An electrooxidation polymerization was carried out within the three-electrode cell. The electrolytic solution was prepared by dissolving 10 millimoles of 1-aminopyrene and a different amount of pyridine in acetonitrile containing 0.1 mol/l of sodium perchlorate acting as a supporting electrolyte. The amount of pyridine was 0, 2, 5, 10, 20 and 100 millimoles, respectively. For performing the electrooxidation polymerization, the linear potential sweep of the working electrode was cycled three times between 0 V and 1 V (vs. SSCE) at a scan rate of 50 mV/sec, followed by holding the potential of the working electrode at +1 V (vs. SSCE) for 10 minutes so as to carry out the desired electrooxidation polymerization. The resultant pH sensors a to f were sufficiently washed with water and, then, subjected to the following experiments.

Experiment 1

Each of the pH sensors a to f was incorporated into the apparatus shown in FIG. 2 so as to provide the pH sensor 10 shown in FIG. 2. The reference electrode 23 shown in the drawing was provided by an SSCE. Also, a potentiometer of a high input impedance was used as the potentiometer 24. Further, a phosphate buffer solution having differing pH values was used as the solution to be measured. Under this condition, the electromotive force (E) of the pH sensor was measured at various pH values of the solution at 25°±0.1° C., with the results as shown in FIG. 3. As seen from FIG. 3, the electromotive force and the pH value were found to give a substantially linear relationship. The slope (mV/pH) of each of the straight lines a to f shown in FIG. 3 is given in Table 1 below:

TABLE 1

| pH sensor (or graph) | Pyridine addition (milli mole/l) | Slope (mV/pH) |
|---|---|---|
| a | 0 | 53 |
| b | 2 | 55 |
| c | 5 | 48 |
| d | 10 | 48 |
| e | 20 | 42 |
| f | 100 | 51 |

Experiment 2

Figure 4:
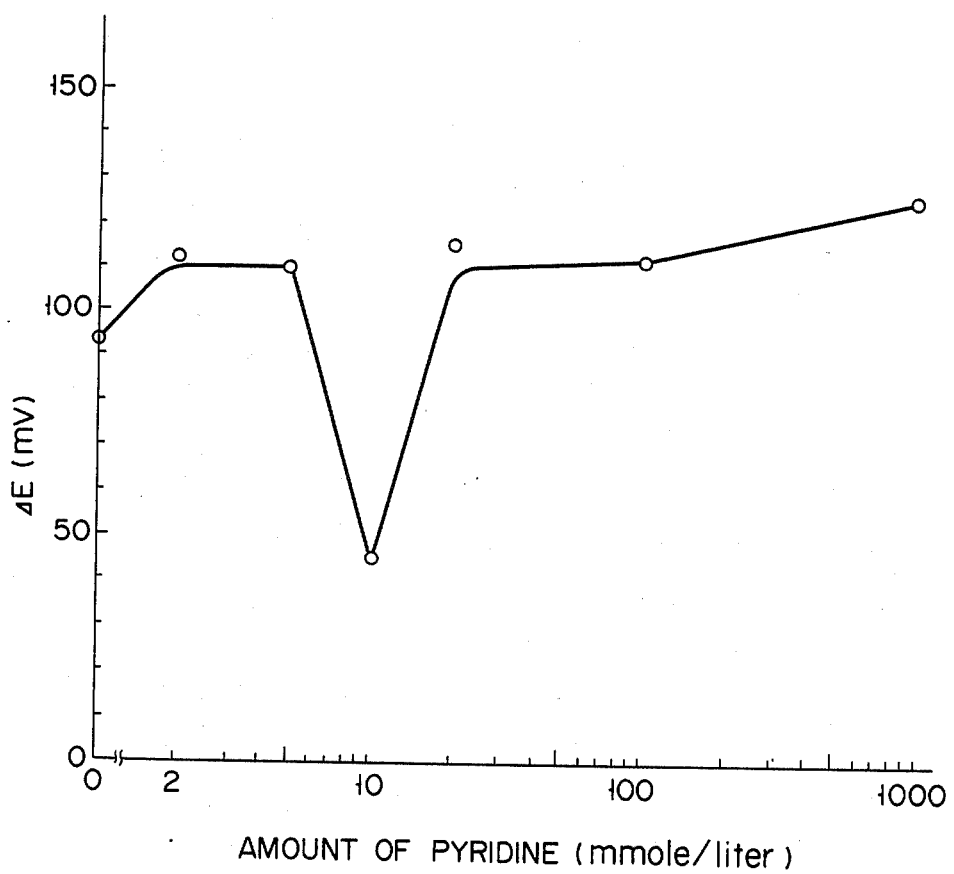

This experiment was intended to examine the effect on the pH sensor given by interfering substances contained in the solution. Specifically, the electromotive force (vs. SSCE) of the pH sensor was measured with respect to both a phosphate buffer solution having a constant pH value of 6.76 and a dog urine. FIG. 4 shows the differences in the electromotive force between the cases of the buffer solution and the dog urine. It is seen that the effect on the pH sensor of the present invention caused by interfering ions contained in the solution to be measured is negligibly small. The difference in the electromotive force is particularly small where the pH sensor is provided with an electrooxidation copolymer containing the same molar amount of 1-aminopyrene and pyridine, i.e., the pH sensor d, indicating that the pH sensor d is particularly unlikely to be affected by the interfering substances even in the dog urine.

Experiment 3

Figure 5:
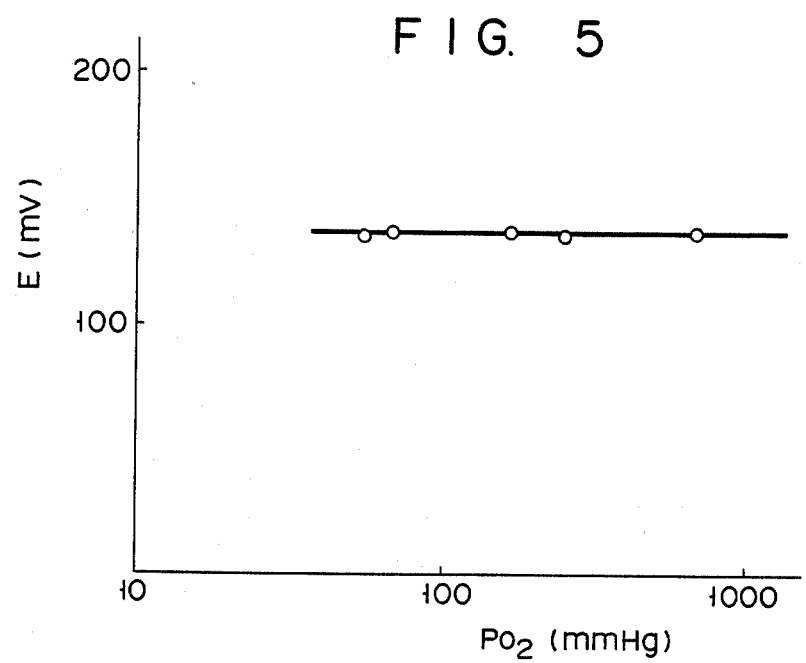

This experiment was intended to examine the effect of oxygen gas on the pH sensor of the present invention. Specifically, a mixture of nitrogen gas and oxygen gas having a total pressure of 760 mm Hg was dissolved by using an artificial lung in a phosphate buffer solution having a constant pH value of 6.30. The electromotive force (vs. SSCE) of the pH sensor d was measured by changing the oxygen partial pressure ($P_{O_2}$) of the gaseous mixture, with the results as shown in FIG. 5. It is seen that the electromotive force was constant regardless of the oxygen gas partial pressure, indicating that the pH sensor of the present invention is not affected by the oxygen dissolved in the solution to be measured.

Figure 6:
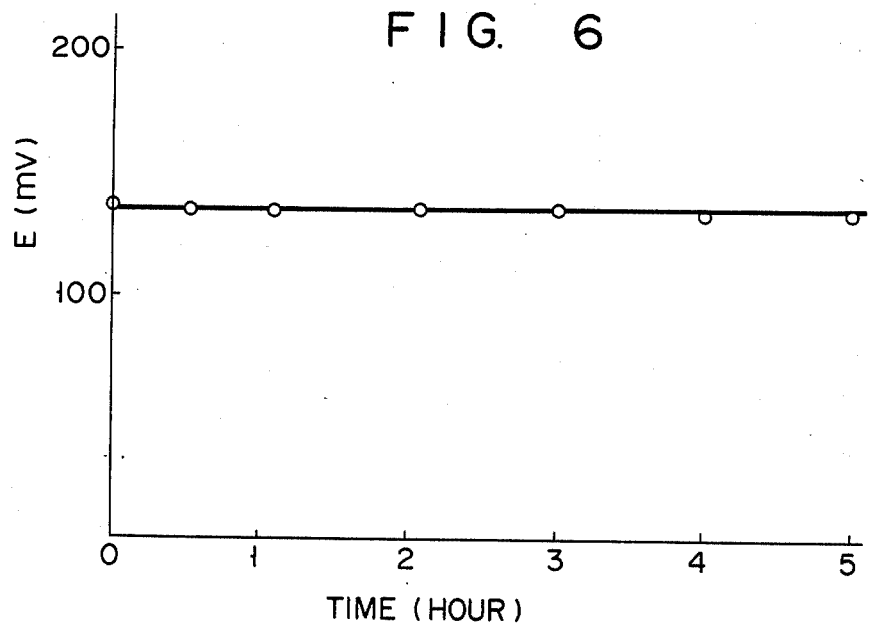

Further, the pH sensor was kept immersed in the solution for 5 hours with the oxygen partial pressure $P_{O_2}$ set at 650 mm Hg. During the immersion, no substantial change was recognized in the electromotive force as shown in FIG. 6.

Experiment 4

The surface of the electrooxidation copolymer layer of the pH sensor d was post-treated under the condition given below, followed by conducting experiments similar to those of Experiments 1 and 2. Table 2 shows the results:

TABLE 2

| Post-Treatment | *          | **       |
|----------------|------------|----------|
| g              | 51 (mV/pH) | 68 (mV)  |
| h              | 45 (mV/pH) | 32 (mV)  |
| i              | 52 (mV/pH) | 62 (mV)  |
| j              | 52 (mV/pH) | 72 (mV)  |
| k              | 46 (mV/pH) | 45 (mV)  |
| l              | 54 (mV/pH) | 63 (mV)  |

*Slope of straight line for Nernst's equation (at 25 ± 0.1° C.)
**Difference in electromotive forces in the phosphate buffer solution and in dog urines.
Post-Treatment:
g... Application of +0.3 V (vs. SSCE) for 30 minutes in a phosphate buffer solution having a pH value of 6.8 (oxidizing treatment)
h... The same as post-treatment g except that the voltage applied was −0.15 V (reducing treatment)
i... The same as post-treatment g except that −0.6 V was kept applied for 15 minutes (reducing treatment)
j... The same as post-treatment g except that −1.99 V was kept applied for 15 minutes (reducing treatment)
k... Immersion in a 5% aqueous solution of $Na_2SO_4$ for 30 hours (reducing treatment)
l... Immersion in a 5% aqueous solution of $NaBH_4$ for 15 hours (reducing treatment)

Table 2 shows that the difference in the electromotive force is particularly small where the electrooxidation polymer is reduced in the post-treatment h, indicating that the pH sensor is less likely to be affected by the interfering substances.

As described above in detail, the pH sensor of the present invention permits accurately measuring the hydrogen ion concentration (pH) of a solution even if the solution contains interfering substances and oxygen dissolved therein.

What is claimed is:

1. A pH sensor comprising:

a substrate formed of an electrically conductive carbon material; and a hydrogen ion-sensitive layer formed on the substrate surface, said hydrogen ion-sensitive layer being formed of an electrooxidation polymer of a nitrogen-containing aromatic compound selected from the group consisting of 1-aminopyrene and a mixture of 1-aminopyrene and pyridine.

2. The pH sensor according to claim 1, wherein said hydrogen ion-sensitive layer is formed of an electrolytic oxidation copolymer consisting of substantially the same molar amount of 1-aminopyrene and pyridine units.

3. The pH sensor according to claim 1, wherein the thickness of the hydrogen ion-sensitive layer ranges between 1 μm and 1 mm.

4. The pH sensor according to claim 1, which further comprises a protective layer formed on the hydrogen ion-sensitive layer, said protective layer being pervious to hydrogen ions.

5. The pH sensor according to claim 4, wherein said protective layer is formed of a material selected from the group consisting of poly(hydroxyethyl methacrylate), nitro cellulose, acetyl cellulose, regenerated cellulose and polycarbonate.

6. The pH sensor according to claim 4, wherein the thickness of the protective layer ranges between 0.1 μm and 300 μm.

7. The pH sensor according to claim 1, which further comprises a protective layer formed on the hydrogen ion-sensitive layer, said protective layer being pervious to hydrogen ions; and the thickness of said protective layer being between 0.1 μm and 300 μm.

8. The pH sensor according to claim 7, wherein said hydrogen ion-sensitive layer is formed of an electrolytic oxidation copolymer consisting of substantially the same molar amount of 1-aminopyrene and pyridine units.

9. The pH sensor according to claim 8 wherein said hydrogen ion-sensitive layer formed of said electrooxidation copolymer is, partially in reduced form.

* * * * *